United States Patent
Dal Molin

(10) Patent No.: US 7,747,331 B2
(45) Date of Patent: Jun. 29, 2010

(54) ACTIVE IMPLANTABLE MEDICAL DEVICE WHICH INCLUDES A CIRCUIT OF RF TELEMETRY

(75) Inventor: Renzo Dal Molin, Chatillon (FR)

(73) Assignee: ELA Medical S.A.S., Montrouge (FR)

( * ) Notice: Subject to any disclaimer, the term of this patent is extended or adjusted under 35 U.S.C. 154(b) by 846 days.

(21) Appl. No.: 11/249,659

(22) Filed: Oct. 12, 2005

(65) Prior Publication Data

US 2006/0100674 A1    May 11, 2006

(30) Foreign Application Priority Data

Oct. 12, 2004   (FR)   ................... 04 10742

(51) Int. Cl.
*A61N 1/00* (2006.01)
(52) U.S. Cl. ..................... 607/60; 323/911
(58) Field of Classification Search ............ 607/12, 607/16, 29–34, 59–61; 128/903, 904; 320/103–104, 320/107–108; 323/911
See application file for complete search history.

(56) References Cited

U.S. PATENT DOCUMENTS

| | | | | |
|---|---|---|---|---|
| 4,599,523 A * | 7/1986 | Pless et al. ........... 307/31 |
| 5,265,588 A * | 11/1993 | Nelson et al. ........... 607/5 |
| 5,447,522 A * | 9/1995 | Chang et al. .......... 607/7 |
| 5,591,212 A * | 1/1997 | Keimel ............... 607/5 |
| 5,674,248 A * | 10/1997 | Kroll et al. .......... 607/5 |
| 5,745,350 A * | 4/1998 | Archer et al. ........ 363/15 |
| 5,757,167 A * | 5/1998 | Arora et al. ......... 323/224 |
| 5,807,397 A | 9/1998 | Barreras |
| 6,426,628 B1 | 7/2002 | Palm |
| 6,434,429 B1 * | 8/2002 | Kraus et al. ......... 607/60 |
| 6,453,198 B1 * | 9/2002 | Torgerson et al. ..... 607/29 |
| 6,456,887 B1 * | 9/2002 | Dudding et al. ...... 607/60 |
| 2002/0068957 A1 | 6/2002 | Wolfe |
| 2002/0183800 A1 * | 12/2002 | Schmidt et al. ...... 607/32 |
| 2003/0155887 A1 * | 8/2003 | Bourilkov et al. .... 320/104 |
| 2004/0158296 A1 * | 8/2004 | Greatbatch et al. ... 607/34 |
| 2004/0225333 A1 * | 11/2004 | Greatbatch et al. ... 607/34 |

FOREIGN PATENT DOCUMENTS

EP    1 062 983 A3    12/2000

\* cited by examiner

*Primary Examiner*—Carl H Layno
*Assistant Examiner*—Jessica Sarcione
(74) *Attorney, Agent, or Firm*—Orrick Herrington & Sutcliffe, LLP

(57) ABSTRACT

An active implantable medical device having an RF telemetry circuit. The device is in particular a stimulation, resynchronization, defibrillation and/or cardioversion device. It includes a principal circuit, an RF telemetry auxiliary circuit and a supply battery for the principal and auxiliary circuits. It is envisaged to have between the supply battery and the auxiliary circuit a regulating circuit including an accumulator of electric power coupled with the auxiliary circuit to deliver a current ready to feed the auxiliary circuit, and a load circuit coupled with the supply battery to maintain the accumulator on a predetermined level of load.

16 Claims, 1 Drawing Sheet

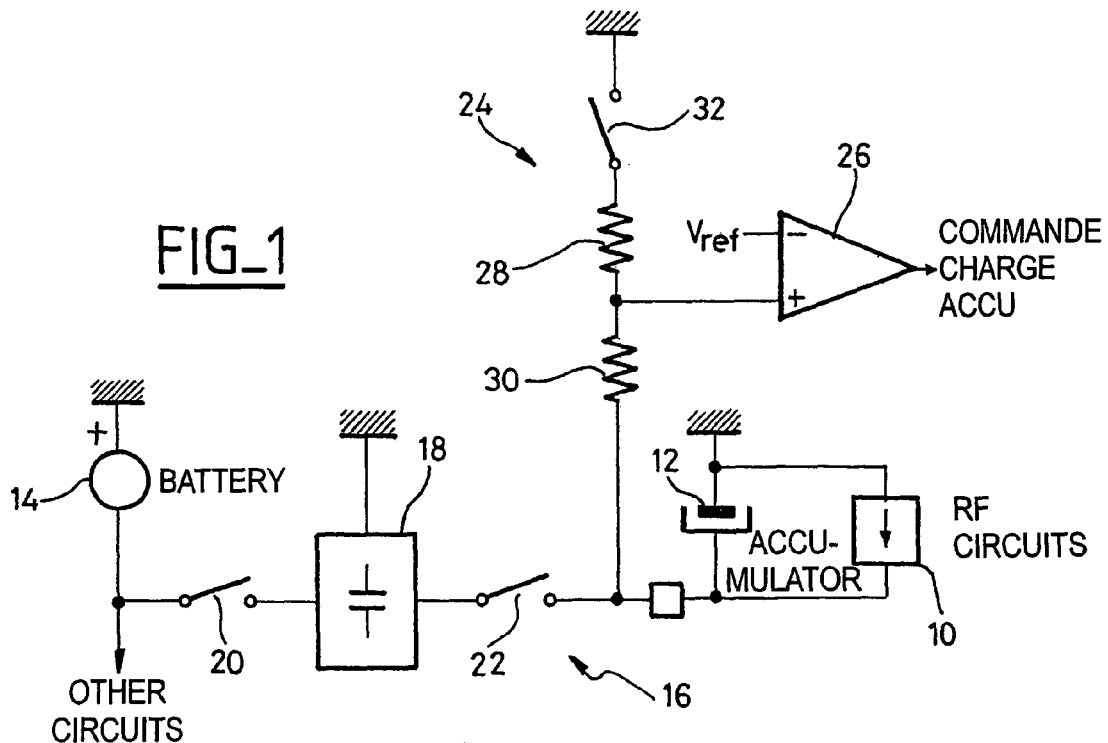
FIG_1
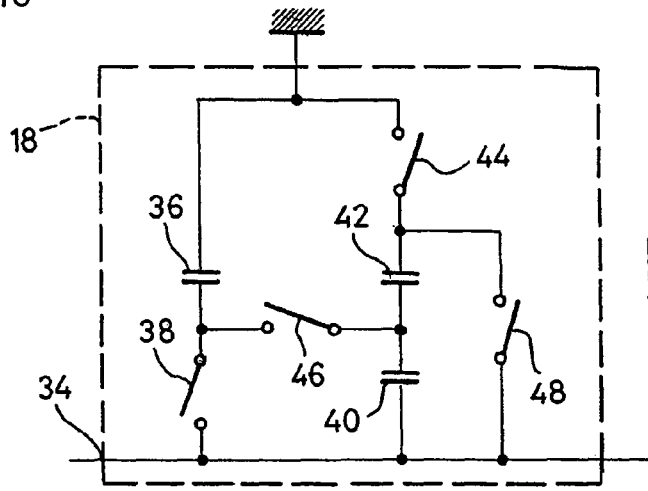
FIG_2
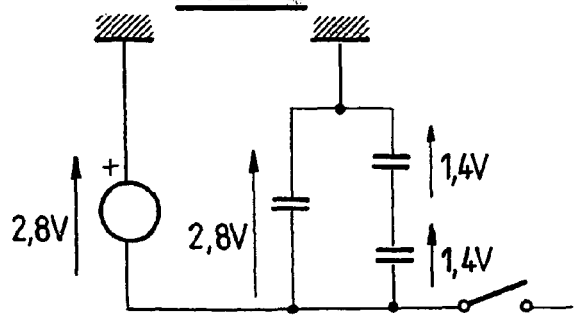
FIG_3
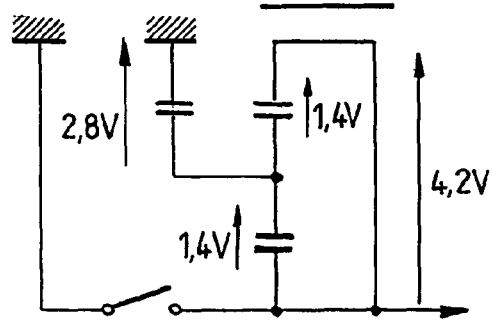
FIG_4

ACTIVE IMPLANTABLE MEDICAL DEVICE WHICH INCLUDES A CIRCUIT OF RF TELEMETRY

FIELD OF THE INVENTION

This invention relates to "active implantable medical devices" as defined by the Jun. 20, 1990 directive 90/385/CEE of the Council of the European Communities.

BACKGROUND OF THE INVENTION

The above-identified definition includes in particular devices that monitor cardiac activity and generate impulses of stimulation, resynchronization, defibrillation, and/or cardioversion in the event the device detects a disorder in heart rate. It also includes, for example, neurological devices, pumps for distribution of medical substances, cochlear implants, and implanted biological sensors, as well as devices for measurement of pH or bio-impedance (such as trans-pulmonary impedance or intracardiac impedance measurements).

With such devices, it is possible to operate a data exchange with a "programmer," which is an external instrument that can be used to check the parameter settings of the devices, to read information recorded by the devices, to register information with the devices, and to update the internal control software of the devices. This data exchange is carried out by telemetry, i.e., by a technique of remote transmission of information, without galvanic contact. Until now, telemetry has primarily been carried out by magnetic coupling between coils in the implanted device and the programmer, which is a technique known as "process by induction." This technique has certain disadvantages, however, because of the low range of an inductive coupling, which necessitates placing a "telemetry head" containing a coil in the vicinity of the implantation site of the active implantable medical device.

Implementation of a different nongalvanic coupling technique has been proposed, using the two components of an electromagnetic wave produced by emitting/receiving circuits operating in the field of radio frequencies (RF), typically at frequencies around a few hundred MHz. This technique, known as RF telemetry, makes it possible to program or interrogate implants at distances greater than 3 meters, and thus carry out information exchanges without having to use a telemetry head, and even without intervention of an external operator. U.S. Patent Application Publication Nos. US2003/0114897 and US2003/0149459 describe implants and programmers equipped with such RF telemetry circuits. These RF circuits require, however, a current supply that is greater than what is necessary for the other circuits of the implant (e.g., the stimulation and detection circuits). For example, the current consumption of an RF circuit can exceed 3 mA during emission phases.

In the case of defibrillators, taking into account the significant amount of current required by circuits used to apply shock therapy, the batteries used have low internal resistance and can supply without difficulty currents of about a few mA. On the other hand, pacemakers and similar devices, such as multisite or resynchronization devices, are generally supplied by small-size lithium-iodine batteries (or their equivalent), taking into account the low operating current required by the stimulation and detection circuits. These batteries have an internal resistance of about 100 Ω at the beginning of their life, which can increase to 1 kΩ, 2 kΩ, or more as the battery discharges. This internal resistance is not a problem for circuits with low consumption, but can prevent one from being able to provide RF circuits with the required level of current.

A first solution is to use a different type of battery, for example, a reduced size lithium-manganese ($LiMnO_2$) weldable button battery with low impedance. There are such batteries whose characteristics are: diameter 12.2 mm, height 1.4 mm, capacity 27 mA/h, nominal voltage 3 V, self-discharge maximum 1% per annum, and which can provide currents of several mA. The current of RF circuits is exclusively provided by the button battery. When the button battery can no longer provide the current, the lithium battery of the pacemaker can provide a low current of 10 μA, which allows the transmitter-receiver to work in pulsated mode. The peak current is provided by a capacitor belonging to a supply circuit controlling the voltage of the battery.

OBJECTS AND SUMMARY OF THE INVENTION

The present invention provides a novel solution to the above-identified problem, which does not require recourse to an additional battery, due to a circuit making it possible to provide to an RF telemetry circuit incorporated in an implant the high current necessary for operation.

For this purpose, the device of the invention, which includes a principal circuit, an auxiliary RF telemetry circuit, and a supply battery for the principal and auxiliary circuits, comprises, between the supply battery and the auxiliary circuit, a regulating circuit including an accumulator of electric power, coupled with the auxiliary circuit to deliver a current ready to feed this auxiliary circuit, and a load circuit coupled with the supply battery to maintain this accumulator with a predetermined level of load. The accumulator can be a rechargeable battery or a condenser. When the voltage corresponding to the predetermined level of load is higher than the voltage delivered by the supply battery, the load circuit includes a voltage multiplying stage.

Advantageously, the load circuit is a circuit with intermittent and cyclic operation. The cyclic report/ratio can be a variable report/ratio function of the internal resistance of the supply battery, with the relative duration of the feeding cycles of the regulating circuit decreasing when the aforementioned resistance or level of load increases. The load circuit can stop the load of the accumulator when the terminal voltage level of the accumulator reaches a predetermined upper limit, when the charging current of the accumulator reaches a predetermined lower limit, or after completion of a given maximum duration.

BRIEF DESCRIPTION OF THE DRAWINGS

One now will describe an example of implementation of the device of the present invention, by reference to the annexed drawings, wherein the same numerical references indicate identical elements from one figure to another and:

FIG. 1 is a simplified circuit diagram of the various elements constituting the feeding circuit of the invention;

FIG. 2 shows details of the voltage multiplier of the circuit of FIG. 1; and

FIGS. 3 and 4 show the charge and discharge configurations of the voltage multiplier of FIG. 2 according to the commutation states of the various switches.

DETAILED DESCRIPTION OF THE INVENTION

One now will describe an embodiment of the device of the invention, which can in particular be applied to the active implantable medical devices marketed by ELA Medical, Montrouge, France, such as the Symphony and Rhapsodybranded devices. These are devices with a programmable microprocessor comprising circuits to receive, format, and treat electric signals collected by implanted electrodes, and to deliver stimulation impulses to those electrodes. Adaptation of these devices to the implementation of the functions of the present invention is deemed to be within the ability of persons of ordinary skill in the art, and will not be described in detail (with regard to its software aspects, the invention can be implemented by suitable programming of the operating software of the pacemaker).

In FIG. 1, reference 10 indicates generally the RF telemetry circuits, which require a relatively high supply current (several mA), in particular during emission phases of the modulated signal. To deliver such a supply current, the invention proposes supplying these RF circuits starting from an accumulator 12, itself charged by the supply battery 14 of the implanted device by means of a regulating circuit 16. The supply battery 14 also supplies other circuits of the device (e.g., the detection and stimulation circuits).

Accumulator 12 can be an accumulator of the lithium-ion type, of which there are models of reduced size having characteristics compatible with the supply requirements for RF circuits in implanted devices, typically: capacity 10 mA/h, internal resistance 25 Ω uninterrupted and 8 Ω into alternate, self-discharge maximum of 15% per annum, and rechargeable 250 times with a maximum loss of capacity of 14%. Such accumulators are in particular manufactured by the company Quallion LLC, Sylmar, Calif., USA. Alternatively, the lithium-ion accumulator can be replaced by a condenser of very strong rated capacity, typically about 1 Farad.

The lithium-ion accumulators present a nominal voltage of 4 V at full load, which can then decrease to a value of about 3 V. Because the lithium-iodine batteries used in cardiac pacemakers have a nominal voltage of about 2.8 V, this voltage is insufficient to charge the accumulator 12 and it is therefore necessary to use an intermediate stage voltage multiplier 18, making it possible to deliver to the accumulator a charging voltage of 2.8V×1.5=4.2 V. This voltage multiplier 18 is connected to the supply battery 14 by a switch 20 and to the accumulator 12 by a switch 22. Its operation, and thus the load of the accumulator 12, is controlled by a control circuit 24, which includes a load checking circuit 26 whose entry is connected to a reference voltage standard $V_{ref}$ and to the point between voltage divider resistors 28, 30, which gives an indication of the terminal voltage of accumulator 12 and is brought into service by closing switch 32.

The internal structure of the voltage multiplier 18 is illustrated in FIG. 2. It includes an entry 34 connected via switch 20 to the supply battery 14, making it possible to charge a first condenser 36 by closing a switch 38. This same entry also makes it possible to charge two condensers 40, 42 assembled in series, by closing a switch 44. In addition, a switch 46 makes it possible to connect the point between condensers 40, 42 to the point between condenser 36 and switch 38. Lastly, a switch 48 makes it possible to short-circuit the circuit formed by condensers 40 and 42.

In the initial phase, corresponding to the configuration of FIG. 3, switches 20, 38, and 44 are closed, while switches 22, 46, and 48 are open. Condenser 36 is thus charged with the voltage of the battery (2.8 V) and condensers 40 and 42 are each charged with half of this voltage (1.4 V). In the subsequent phase, switches 20, 38, and 44 are opened, while switches 22, 46, and 48 are closed. Condensers 40 and 42 are then in parallel, and the voltage on their terminals (1.4 V) is added to the boundaries of condenser 36 (2.8 V), thus giving an exit voltage of 2.8+1.4=4.2 V. This voltage of 4.2 V produced by the voltage multiplier 18 is used to charge accumulator 12, with a charging current which can vary from 2 to 0.1 mA, for example, according to changes in the internal resistance of the battery 14.

Advantageously, this load of the accumulator 12 is operated in an intermittent and cyclic way, for example, with a 25% load during a cycle of 1 second, the remaining 75% being devoted to the supply of the other circuits (e.g. the detection and stimulation circuits) of the device.

Advantageously, the cyclic report/ratio (25% in the example above) is a variable report/ratio, a function of the internal resistance of the supply battery 14 (the duration of the phases of load becoming shorter when internal resistance increases) and/or of the load level of accumulator 12 (the duration of the cycles of load decreasing as the accumulator 12 approaches its level of maximum loading).

The load of the accumulator 12 continues thus until reaching a predetermined level, for example, when the load checking circuit 26 detects that the terminal voltage of the accumulator has reached 4 V. The load checking circuit 26 then operates to suspend the load until the terminal voltage of the accumulator 12 has fallen below a given threshold due to energy consumption by the RF circuits.

The load also can be stopped according to other criteria, for example, when the charging current reaches a low limit because of accumulator 12, or at the end of a given maximum duration, for example, at the end of 100 hours for 10 mA of charging current.

RF circuits 10, supplied with the energy stored in accumulator 12, could be fed satisfactorily with a relatively significant output current, for example from 3 to 20 mA.

To take into account the difference between the terminal voltage of the accumulator (about 3 to 4 V according to the level of load) and the level of nominal voltage required for the supply of RF components (typically between 1.8 and 3 V), use of an adapted regulator is envisaged, for example, a linear or self-inductive regulator, to generate the supply voltage wanted with a suitable capacity while running.

One skilled in the art will appreciate that the present invention can be practiced by other than the described embodiments which are presented for purposes of illustration and not of limitation.

I claim:

1. An active implantable medical device, comprising:
   a principal circuit;
   an auxiliary RF telemetry circuit;
   a supply battery having an internal resistance;
   a voltage multiplying stage comprising a plurality of condensers connected by a plurality of switches for multiplying a voltage delivered by the supply battery by charging the plurality of condensers; and
   a regulating circuit comprising an accumulator, the accumulator having a load level and being connected to a load circuit,
   wherein the supply battery, while providing power to the principal circuit with a first voltage, charges the plurality of condensers of the voltage multiplying stage during a first phase of a variable period and charges the accumulator to a second voltage by changing connectivity among the plurality of condensers using the plurality of switches during a second phase of the variable period;
   wherein the load circuit detects a terminal voltage of the accumulator; and
   wherein the accumulator delivers power with the second voltage to the auxiliary RF telemetry circuit, and the load circuit maintains the accumulator at a predetermined load level by varying the variable period and/or controlling at least one switch of the plurality of switches of the regulating circuit in response to the detected terminal voltage of the accumulator.

2. The device of claim 1, wherein said accumulator is a rechargeable battery.

3. The device of claim 1, wherein said accumulator is a condenser.

4. The device of claim 1, wherein a voltage corresponding to the predetermined load level is higher than the voltage delivered by the supply battery.

5. The device of claim 4, wherein the voltage multiplying stage delivers an exit voltage higher than the voltage delivered by the supply battery to the accumulator.

6. The device of claim 1, wherein the load circuit is configured for intermittent and cyclic operation having a cyclic report/ratio.

7. The device of claim 6, wherein the cyclic report/ratio is a variable report/ratio function of the internal resistance of the supply battery, and wherein a relative duration of the variable period of the time cycle decreases when the internal resistance increases.

8. The device of claim 6, wherein the cyclic report/ratio is a variable report/ratio function of the load level of the accumulator, and wherein a relative duration of the variable period of the time cycle decreases when the load level increases.

9. The device of claim 1, wherein the load circuit can stop the load of the accumulator when a level of terminal voltage of the accumulator reaches a predetermined upper limit.

10. The device of claim 1, wherein the load circuit can stop the load of the accumulator when a charging current of the accumulator reaches a predetermined lower limit.

11. The device of claim 1, wherein the load circuit can stop the load of the accumulator after completion of a given maximum duration.

12. The device of claim 1, wherein the plurality of condensers comprises a first condenser, a serial condenser comprising a second condenser and a third condenser, wherein, during the first phase of the variable period, the first condenser is parallelly connected to the serial condenser between a ground terminal and a high voltage terminal, the second condenser and the third condenser of the serial condenser are serially connected at a midpoint, and the high voltage terminal of the serial condenser is connected to the high voltage terminal of the supply battery using a first switch of the plurality of switches, and wherein, during the second phase of the variable period, the ground terminal of the first condenser is connected to the midpoint of the serial condenser using a second switch of the plurality of switches, and the high voltage terminal of the serial condenser is opened using the first switch of the plurality of the switches.

13. The device of claim 1, wherein the load circuit comprises a comparator and a plurality of serially connected voltage divider resistors.

14. The device of claim 13, wherein the comparator compares the terminal voltage of the accumulator with a reference voltage.

15. The device of claim 14, wherein the regulating circuit stops charging the accumulator if the terminal voltage of the accumulator reaches an upper threshold voltage.

16. The device of claim 14, wherein the regulating circuit resumes charging the accumulator if the terminal voltage of the accumulator falls below a lower threshold voltage.

\* \* \* \* \*